US012615427B2

(12) United States Patent
Feingold et al.

(10) Patent No.: US 12,615,427 B2
(45) Date of Patent: Apr. 28, 2026

(54) VISIBLE FLUORESCENT VIEWING SYSTEM

(71) Applicant: Stryker Corporation, Kalamazoo, MI (US)

(72) Inventors: Benjamin Hyman Feingold, San Francisco, CA (US); Marc André, Spiegel b. Bern (CH); West Mitchell, San Jose, CA (US)

(73) Assignee: Stryker Corporation, Portage, MI (US)

( * ) Notice: Subject to any disclaimer, the term of this patent is extended or adjusted under 35 U.S.C. 154(b) by 148 days.

(21) Appl. No.: 18/528,490

(22) Filed: Dec. 4, 2023

(65) Prior Publication Data

US 2024/0196077 A1    Jun. 13, 2024

Related U.S. Application Data

(60) Provisional application No. 63/386,881, filed on Dec. 9, 2022.

(51) Int. Cl.
H04N 23/56 (2023.01)
A61B 5/00 (2006.01)
(Continued)

(52) U.S. Cl.
CPC ........... H04N 23/56 (2023.01); A61B 5/0071 (2013.01); G02F 1/13318 (2013.01);
(Continued)

(58) Field of Classification Search
CPC .... H04N 23/56; H04N 23/661; H04N 23/667; A61B 5/0071; A61B 1/0638;
(Continued)

(56) References Cited

U.S. PATENT DOCUMENTS

2006/0004292 A1    1/2006  Beylin
2008/0129900 A1    6/2008  Sharp et al.
(Continued)

FOREIGN PATENT DOCUMENTS

JP        2022509460 A  *  1/2022
WO            99/37204 A1    7/1999
(Continued)

OTHER PUBLICATIONS

International Preliminary Report on Patentability mailed Jun. 19, 2025, directed to International Application No. PCT/US2023/082335; 8 pages.
(Continued)

*Primary Examiner* — Nasim N Nirjhar
(74) *Attorney, Agent, or Firm* — Morrison & Foerster LLP

(57)                ABSTRACT

Disclosed herein are viewing systems configured for viewing an image of a biological object illuminated with light and a viewing device (e.g., loupes, glasses, etc.) and methods for operation thereof. The viewing device comprises a plurality of viewing modes: a white light mode, a fluorescent light mode, and an overlay mode, and a shutter that opens and closes in accordance with the viewing mode. An overlay image is an image of the biological object when the biological object is illuminated with both white light and fluorescent light, causing the overlay image to be an overlay of the white light image and the fluorescent light image. The disclosed systems and methods allow a user (e.g., a surgeon, medical staff, etc.) to preserve the ergonomics offered by eyewear while providing fluorescent viewing capabilities, particularly with visible fluorescent dyes.

20 Claims, 8 Drawing Sheets

(51) Int. Cl.

| | |
|---|---|
| *G02F 1/133* | (2006.01) |
| *G02F 1/137* | (2006.01) |
| *G03B 7/08* | (2021.01) |
| *G03B 9/08* | (2021.01) |
| *H04N 23/661* | (2023.01) |
| *H04N 23/667* | (2023.01) |

(52) U.S. Cl.

CPC .............. *G02F 1/137* (2013.01); *G03B 7/08* (2013.01); *G03B 9/08* (2013.01); *H04N 23/661* (2023.01); *H04N 23/667* (2023.01)

(58) Field of Classification Search

CPC ..... A61B 1/0692; A61B 90/20; A61B 90/361; A61B 2017/00154; A61B 2017/00221; A61B 2017/00734; A61B 2090/304; A61B 2090/309; A61B 2090/3616; A61B 2090/372; A61B 2090/502; A61B 1/043; A61B 90/30; G02F 1/13318; G02F 1/137; G03B 7/08; G03B 9/08; H05B 47/105; H05B 47/155; H05B 47/16; G02B 21/0012; G02B 21/16

See application file for complete search history.

(56) References Cited

U.S. PATENT DOCUMENTS

| | | | |
|---|---|---|---|
| 2019/0029090 A1 | 1/2019 | Ikehara et al. | |
| 2020/0345204 A1* | 11/2020 | Granneman | ....... A61B 1/00045 |
| 2021/0015350 A1 | 1/2021 | Butte et al. | |
| 2021/0038339 A1 | 2/2021 | Yu et al. | |
| 2021/0120193 A1* | 4/2021 | Swager | ................. C09K 11/06 |

FOREIGN PATENT DOCUMENTS

| | | |
|---|---|---|
| WO | 2015/185661 A1 | 12/2015 |
| WO | 2019/014205 A1 | 1/2019 |

OTHER PUBLICATIONS

International Search Report and Written Opinion mailed Apr. 12, 2024, directed to International Application No. PCT/US2023/082335; 10 pages.

* cited by examiner

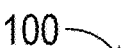
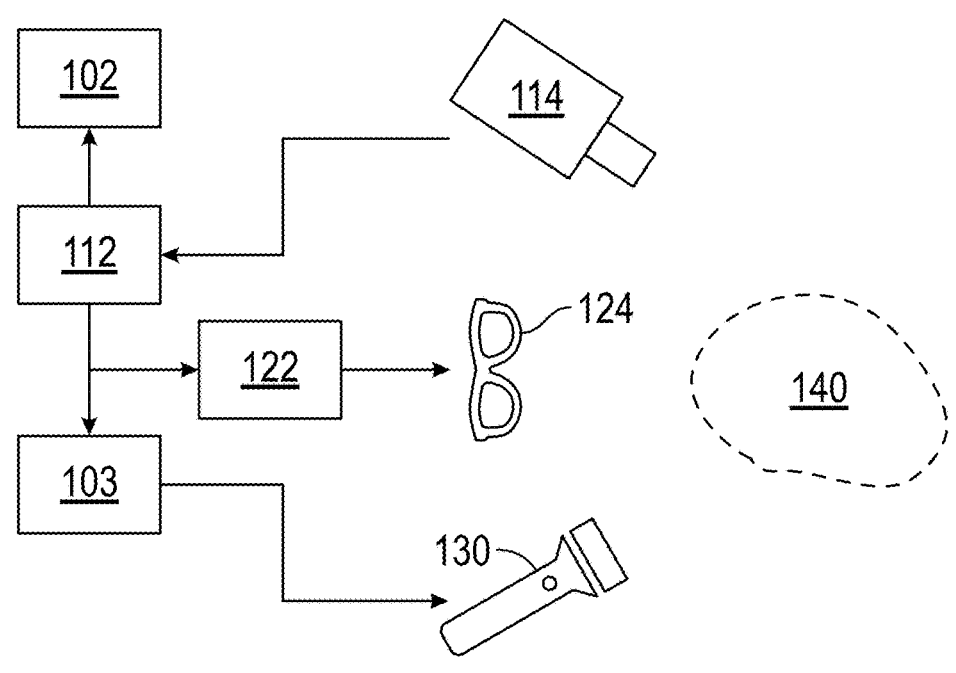
FIG. 1A
FIG. 1B

VISIBLE FLUORESCENT VIEWING SYSTEM

CROSS-REFERENCE TO RELATED APPLICATIONS

This application claims the benefit of U.S. Provisional Application No. 63/386,881, filed Dec. 9, 2022, the entire contents of which are hereby incorporated by reference herein.

FIELD

The present invention relates to a viewing device capable of viewing an image of a biological object exposed to a visible fluorescent dye during a surgical procedure.

BACKGROUND

There are different forms of intraoperative optical imaging used in surgical procedures, such as fluorescent viewing. Fluorescent viewing devices have been incorporated into a variety of specialized imaging equipment tailored for particular surgical applications, such as, for example, surgical microscopes or open field imaging systems. Fluorescent viewing allows a user to visualize different structures and tissues (e.g., blood perfusion) during the surgical procedure that may not be observable under other lighting conditions.

A fluorescent viewing device may be configured to detect the excitation wavelength(s) of a corresponding fluorophore. One example type of fluorescent viewing involves the use of indocyanine green (ICG), which is an infrared fluorescent dye that is commonly used for surgical procedures. Although ICG may be useful for some anatomical visualization, some surgical procedures may benefit from using other types of fluorescent dyes. For example, visible fluorescent dyes may be useful for nerve visualization for head and neck surgery. However, one challenge with using a visible fluorescent dye is the excitation and emission spectra are visible to the human eye. The common spectra between the visible fluorescence and the background (white light) may make it difficult to differentiate between the two, particularly when viewing an image of the biological object using a viewing device, such as loupes or glasses.

SUMMARY

According to various aspects, the viewing systems of the present disclosure are configured for viewing an image of a biological object illuminated with light and a viewing device (e.g., loupes, glasses, etc.). The viewing device comprises a plurality of viewing modes: a white light mode, a fluorescent light mode, and an overlay mode, and a shutter that opens and closes in accordance with the viewing mode. In the white light mode, the biological object is illuminated with white light and the viewing device views a white light image of the biological object. In the fluorescent light mode, the biological object is illuminated with fluorescent light for exciting a fluorophore, such as a fluorescent dye, in the biological object, and the viewing device views a fluorescent light image emitted by the fluorophore in the biological object. An overlay image is an image of the biological object when the biological object is illuminated with both white light and fluorescent light, causing the overlay image to be an overlay of the white light image and the fluorescent light image. The disclosed systems and methods allow a user (e.g., a surgeon, medical staff, etc.) to preserve the ergonomics offered by eyewear while providing fluorescent viewing capabilities, particularly with visible fluorescent dyes (fluorescent dyes having emission spectra, and optionally excitation spectra, that are visible to the human eye).

According to some examples, a viewing system for viewing an image of a biological object comprises: a light source for illuminating the biological object with light; and a viewing device that views the image of the biological object when the biological object is illuminated with the light, wherein the viewing device comprises a shutter that opens and closes in accordance with a viewing mode of the viewing device.

Optionally, the viewing system comprises: a light source for illuminating the biological object with fluorescent light for exciting a fluorescent dye in the biological object, and the viewing device is configured for viewing the image of the biological object as a result of fluorescent light emitted by the fluorescent dye in the biological object. The fluorescent light for exciting the fluorescent dye and/or the emitted fluorescent light can be visible fluorescent light.

In any of the examples, the viewing device comprises glasses, one or more loupes, a microscope, or a corresponding clip-on device. In any of the examples, the viewing device can comprise eyewear.

In any of the examples, the shutter is an electronic shutter.

In any of the examples, the shutter is a liquid crystal shutter.

In any of the examples, the shutter is disposed within the viewing device.

In any of the examples, an open time of the shutter varies based on the viewing mode.

In any of the examples, the viewing mode comprises a white light mode, a fluorescent light mode, and an overlay mode.

In any of the examples, when the viewing mode is a white light mode, the shutter is open during a white light pulse. In any of the examples, when the viewing mode is a white light mode, the shutter can be closed for a first portion of a white light pulse and open for a second portion of the white light pulse.

In any of the examples, when the viewing mode is a white light mode, the shutter is closed during a fluorescent light pulse.

In any of the examples, when the viewing mode is a fluorescent light mode, the shutter is open during a fluorescent light pulse.

In any of the examples, when the viewing mode is a fluorescent light mode, the shutter is closed during a white light pulse.

In any of the examples, when the viewing mode is an overlay mode, the shutter is open for a white light pulse and a fluorescent light pulse.

In any of the examples, when the viewing mode is an overlay mode, the shutter is open for a portion of a white light pulse.

In any of the examples, one or more of: an open time of the shutter, an amount of white light in an overlay image, an amount of fluorescent light in the overlay image, or a combination thereof, are dynamically adjustable.

In any of the examples, a brightness of the light is dynamically adjustable by increasing or decreasing one or more of: an on-time of the light source, an intensity of the light source, an open time of the shutter, or a combination thereof.

In any of the examples, the viewing device comprises a filter that blocks an excitation wavelength from transmitting through the viewing device. The excitation wavelength can be the wavelength of the fluorescent light for exciting the fluorescent dye.

In any of the examples, the system further comprises: a viewing device controller that controls operation of the viewing device, wherein the viewing device comprises a wireless transceiver that communicatively couples the viewing device and the viewing device controller.

In any of the examples, the system further comprises: a viewing device controller that controls operation of the viewing device, wherein the viewing device comprises a cable that communicatively couples the viewing device and the viewing device controller.

In any of the examples, the light source comprises an infrared light source.

In any of the examples, the light source comprises an infrared light source, the system further comprises: a viewing device controller that generates pulses for the infrared light source, wherein the viewing device uses the pulses for synchronizing with the light source.

In any of the examples, the system further comprises: a capture device comprising a camera that captures the image of the biological object when the biological object is illuminated with the light.

In any of the examples, the system further comprises: a capture device comprising: a camera that captures the image of the biological object when the biological object is illuminated with the light; and a display that displays the image of the biological object captured by the camera.

In any of the examples, the system further comprises: a capture device comprising: a camera that captures the image of the biological object when the biological object is illuminated with the light; and a camera controller that controls operation of the camera.

In any of the examples, the system further comprises: a hands-free device that receives an input corresponding to a selection of the viewing mode.

In any of the examples, the system further comprises: a hands-free device that receives an input corresponding to a selection of the viewing mode, wherein the hands-free device comprises a foot switch or a voice command system.

In any of the examples, the system further comprises: an input device that receives an input corresponding to settings for the viewing mode.

In any of the examples, the system further comprises: a database comprising a user profile including settings for the viewing mode.

In any of the examples, settings of the viewing mode are dynamically adjustable, the settings comprising one or more of: an illumination intensity of white light, an illumination intensity of fluorescent light, an on-time of a white light source, an on-time of a fluorescent light source, an open time of the shutter, a close time of the shutter, an amount of white light in an overlay image, an amount of fluorescent light in an overlay image, a number of times the shutter opens during a frame, or a combination thereof.

In any of the examples, the light source comprises a white light source and a fluorescent light source.

In any of the examples, the light comprises white light and fluorescent light.

In any of the examples, the light source comprises a blue light source and a red-green light source.

In any of the examples, the system further comprises: a second viewing device that views the image of the biological object when the biological object is illuminated with the light, wherein the second viewing device comprises a second shutter that opens and closes in accordance with a second viewing mode of the second viewing device.

In any of the examples, the system further comprises: a second viewing device that views the image of the biological object when the biological object is illuminated with the light, wherein the second viewing device comprises a second shutter that opens and closes in accordance with a second viewing mode of the second viewing device, wherein the viewing mode of the viewing device is capable of being different from the second viewing mode of the second viewing device.

According to some examples, a method of viewing an image of a biological object comprises: illuminating, using a light source, the biological object with light; viewing, by a viewing device, an image of the biological object when the biological object is illuminated with the light; and opening and closing a shutter of the viewing device in accordance with a viewing mode of the viewing device.

In any of the examples, the viewing device comprises glasses, one or more loupes, a microscope, or a corresponding clip-on device. In any of the examples, the viewing device can comprise eyewear.

In any of the examples, the shutter is an electronic shutter.

In any of the examples, the shutter is a liquid crystal shutter.

In any of the examples, the shutter is disposed within the viewing device.

In any of the examples, the method further comprises: adjusting an open time of the shutter based on the viewing mode.

In any of the examples, the viewing mode comprises a white light mode, a fluorescent light mode, and an overlay mode. In the white light mode, the biological object is illuminated with white light and the method comprises viewing, by the viewing device, a white light image of the biological object. In the fluorescent light mode, the biological object is illuminated with fluorescent light for exciting a fluorophore, such as a fluorescent dye, in the biological object, and the method comprises viewing, by the viewing device, a fluorescent light image emitted by the fluorophore in the biological object. In the overlay mode, the biological object is illuminated with both white light and fluorescent light, and the method comprises viewing, by the viewing device, an overlay image being an overlay of the white light image and the fluorescent light image.

In any of the examples, when the viewing mode is a white light mode, the shutter is closed for a first portion of a white light pulse and open for a second portion of the white light pulse.

In any of the examples, when the viewing mode is a white light mode, the shutter is open during a white light pulse. In any of the examples, when the viewing mode is a white light mode, the shutter can be closed during a fluorescent light pulse.

In any of the examples, when the viewing mode is a fluorescent light mode, the shutter is open during a fluorescent light pulse.

In any of the examples, when the viewing mode is a fluorescent light mode, the shutter is closed during a white light pulse.

In any of the examples, when the viewing mode is an overlay mode, the shutter is open for a white light pulse and a fluorescent light pulse.

In any of the examples, when the viewing mode is an overlay mode, the shutter is open for a portion of a white light pulse.

In any of the examples, the method further comprises: dynamically adjusting one or more of: an open time of the shutter, an amount of white light in an overlay image, an amount of fluorescent light in the overlay image, or a combination thereof.

In any of the examples, the method further comprises: dynamically adjusting a brightness of the light by increasing or decreasing one or more of: an on-time of the light source, an intensity of the light source, an open time of the shutter, or a combination thereof.

In any of the examples, the method further comprises: filtering the light such that an excitation wavelength is blocked from transmitting through the viewing device. The excitation wavelength can be the wavelength of the fluorescent light for exciting the fluorescent dye.

In any of the examples, the method further comprises: communicating a signal between a viewing device controller and the viewing device via a wireless connection, wherein the viewing device controller controls operation of the viewing device.

In any of the examples, the method further comprises: communicating a signal between a viewing device controller and the viewing device via a cable, wherein the viewing device controller controls operation of the viewing device.

In any of the examples, the method further comprises: illuminating, using the light source, infrared light.

In any of the examples, the method further comprises: generating pulses for an infrared light source of the light source; and synchronizing the viewing device and the light source using the pulses.

In any of the examples, the method further comprises: capturing, by a capture device, the image of the biological object when the biological object is illuminated with the light.

In any of the examples, the method further comprises: capturing, by a capture device, the image of the biological object when the biological object is illuminated with the light; and displaying, by a display, the image of the biological object captured by the camera.

In any of the examples, the method further comprises: receiving an input corresponding to a selection of the viewing mode from a hands-free device.

In any of the examples, the method further comprises: receiving an input corresponding to a selection of the viewing mode from a hands-free device; and switching the viewing mode in response to the input.

In any of the examples, the method further comprises: receiving settings for the viewing mode from an input device.

In any of the examples, the method further comprises: receiving settings for the viewing mode from a profile.

In any of the examples, the method further comprises: dynamically adjusting settings for the viewing mode, wherein the settings comprise one or more of: an illumination intensity of white light, an illumination intensity of fluorescent light, an on-time of a white light source, an on-time of a fluorescent light source, an open time of the shutter, a close time of the shutter, an amount of white light in an overlay image, an amount of fluorescent light in an overlay image, or a number of times the shutter opens during a frame.

In any of the examples, illuminating the biological object comprises: illuminating, using a white light source, the biological object with white light; and illuminating, using a fluorescent light source, the biological object with fluorescent light.

In any of the examples, the light comprises white light and fluorescent light.

In any of the examples, illuminating the biological object comprises: illuminating, using a blue light source, the biological object with blue light; and illuminating, using a red-green light source, the biological object with red and green light.

In any of the examples, the method further comprises: viewing, using a second viewing device, the image of the biological object when the biological object is illuminated with the light; and opening and closing a second shutter of the second viewing device in accordance with a second viewing mode of the second viewing device.

In any of the examples, the method further comprises: viewing, using a second viewing device, the image of the biological object when the biological object is illuminated with the light; and opening and closing a second shutter of the second viewing device in accordance with a second viewing mode of the second viewing device, wherein the viewing mode of the viewing device is capable of being different from the second viewing mode of the second viewing device.

According to some examples, an apparatus comprises a viewing device that views an image of a biological object when the biological object is illuminated with light, wherein the viewing device comprises a shutter that opens and closes in accordance with a viewing mode of the viewing device.

In any of the examples, the viewing device comprises glasses, one or more loupes, a microscope, or a corresponding clip-on device. In any of the examples, the viewing device can comprise eyewear.

It will be appreciated that any of the variations, aspects, features, and options described in view of the systems apply equally to the methods and apparatus, and vice versa. It will also be clear that any one or more of the above variations, aspects, features, and options can be combined.

BRIEF DESCRIPTION OF THE FIGURES

The invention will now be described, by way of example only, with reference to the accompanying drawings, in which:

FIG. 1A illustrates an example viewing system, according to some aspects.

FIG. 1B illustrates an example configuration of a viewing device, according to some aspects.

DETAILED DESCRIPTION

Figure 1C:
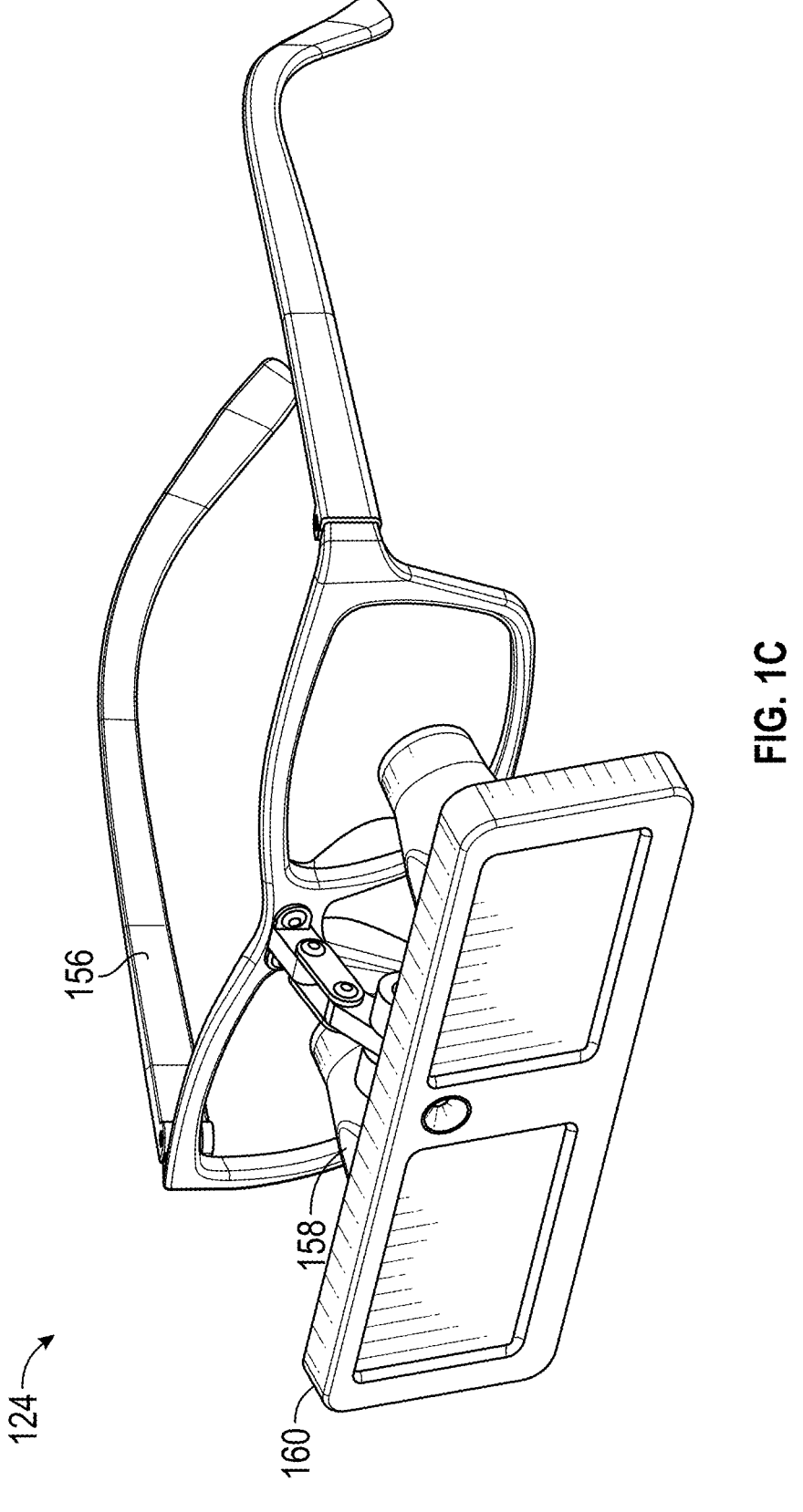
FIG. 1C and FIG. 1D illustrate an example viewing system comprising a clip-on device, according to some aspects.

Reference will now be made in detail to implementations and various aspects and variations of systems and methods described herein. Although several example variations of the systems and methods are described herein, other variations of the systems and methods may include aspects of the systems and methods described herein combined in any suitable manner having combinations of all or some of the aspects described.

Systems and methods according to the principles described herein allow a user (e.g., a surgeon, medical staff, etc.) to view an image of a biological object exposed to a visible fluorescent dye during a surgical procedure using a viewing device. The visible fluorescent dye has an emission spectrum, and optionally an excitation spectrum, that is visible to the human eye. The fluorescent dye can be pre-administered prior to start of the viewing method. The viewing device may comprise a device (e.g., eyewear, such as glasses, loupes, etc.) worn by the user that allows the user to view the image of the biological object in a plurality of viewing modes: a white light mode where white light illuminates the biological object; a fluorescent light mode where fluorescent light illuminates the biological object; and an overlay mode where white light and fluorescent light illuminate the biological object. The viewing device comprises a shutter that operates in accordance with the viewing mode. In the white light mode, the shutter is open during at least a portion of the white light pulse and closed during the fluorescent light pulse. In the fluorescent light mode, the shutter is closed during the white light pulse, but open during at least a portion of the fluorescent light pulse. In the overlay mode, the shutter is open during at least a portion of the white light pulse and during at least a portion of the fluorescent light pulse. The viewing system may comprise one or more input devices (e.g., a foot switch) that receives an input corresponding to user's selection of the viewing mode.

In the following description, it is to be understood that the singular forms "a," "an," and "the" used in the following description are intended to include the plural forms as well, unless the context clearly indicates otherwise. It is also to be understood that the term "and/or" as used herein refers to and encompasses any possible combination and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating," or the like, refer to the action and processes of a computer system, or similar electronic computing device, that manipulates and transforms data represented as physical (electronic) quantities within the computer system memories or registers or other such information storage, transmission, or display devices.

The present disclosure in some examples also relates to a device for performing the operations herein. This device may be specially constructed for the required purposes, or it may comprise a general-purpose computer selectively activated or reconfigured by a computer program stored in the computer. Such a computer program may be stored in a non-transitory, computer-readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMS, EEPROMs, magnetic or optical cards, application-specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. Suitable processors include central processing units (CPUs), graphical processing units (GPUs), field-programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

FIG. 1A illustrates an example viewing system, according to some aspects. The viewing system 100 comprises one or more of: a light source 130, a light source controller 103, a camera 114, a camera controller 112, a viewing device 124, a viewing device controller 122, and a display 102. The viewing system 100 is used by, e.g., a user for viewing an image of a biological object 140 (e.g., tissue).

The light source 130 illuminates the biological object 140 with light. For example, the light source 130 may emit white light and/or fluorescent light. The light comprises light patterns emitted from the light source 130. The fluorescent light emitted by the light source 130 causes the biological object 140 to emit fluorescent light. In some aspects, the light source 130 comprises other components such as a lens for directing the white light and/or fluorescent light to the biological object 140. The light source 130 may be a standalone unit or part of a second light source, such as surgical lights in an operating room. The light source 130 comprises solid state light sources (e.g., LEDs, laser diodes, etc.) and/or non-solid state light sources.

The light source 130 emits visible (white) light using one or more color light sources that in combination generate white light, or may include one or more white light sources. In a non-limiting example, the light source 130 includes a combination of discrete color solid state light sources, such as red, green, and blue LEDs and/or lasers, or white LEDs. In some aspects, the light source 130 comprises a blue light source and a red-green light source. As another example, the light source 130 may include a broad spectrum non-solid state source such as an arc lamp combined with a color filter.

The light source 130 also emits light for fluorescent light. In some aspects, the light source 130 comprises different light sources for emitting white light and fluorescent light. Alternatively, the same light source 130 is used to emit white light and fluorescent light, and a filter (e.g., a narrowband filter) is used to select a narrow spectrum of light for the fluorescent light. The light source controller 103 controls operation of the light source 130 based on one or more properties, such as wavelength(s) of the light, on-time of the light source, off-time of the light source, intensity of the light source, etc. In some aspects, the light source controller 103 controls the shutter 128.

The biological object 140 includes any suitable substance or material to be imaged. A fluorescent dye may be administered to the biological object 140. The fluorescent dye then travels to the structure or tissue of interest, which fluoresces when exposed to fluorescent light having the appropriate wavelength. The fluorescent dye may be administered to the biological object 140 prior to viewing the image of the biological object 140.

The viewing device 124 views the image of the biological object 140 when the biological object 140 is illuminated with the light (illuminated from the light source 130). The viewing device 124 comprises glasses, one or more loupes, or a microscope. In this example, the viewing device 124 comprises eyewear. In some aspects, the viewing device 124 includes a lens, notch filter, and/or shutter disposed within the viewing device 124, as shown in the example configuration of FIG. 1B. The lens 126, notch filter 127, and shutter 128 (if included) may be located in the optical path (shown in FIG. 1B) between the biological object 140 being viewed and the human eye. Although the figure illustrates a specific sequence for the lens 126, notch filter 127, and shutter 128, aspects of the disclosure comprise any sequence and/or combination suitable for viewing the biological object 140 using the viewing device 124. Unless otherwise noted, viewing an "image" includes, but is not limited to, viewing a biological object in a direct path from the human eye through the viewing device and to the biological object, such as shown in FIG. 1B.

In instances where the viewing system 100 comprises a microscope, the shutter 128 may be located along the optical path between the biological object 140 and the microscope. For example, the shutter 128 may be located within or mounted to the microscope. In some aspects, the shutter 128 may be located between the user's eyes and the microscope.

The lens 126 magnifies, adjusts the focus point, or otherwise modifies the image of the biological object 140. The notch filter 127 blocks certain wavelengths of light, such as the excitation wavelength, thereby preventing it from transmitting through the viewing device 124.

The shutter 128 may be any type of shutter that opens and closes, allowing or blocking, respectively, the optical path between the biological object 140 and viewing device 124. The shutter 128 opens and closes in accordance with a viewing mode of the viewing device 124. The viewing device 124 may be synchronized with the light source 130. As one non-limiting example, the shutter 128 may be an electronic shutter, such as a liquid crystal shutter. A liquid crystal shutter comprises a plurality of polarizers with liquid crystals located between the polarizers and/or one or more substrates. The liquid crystal shutter allows light to pass from the biological object 140 to the user's eyes in response to an applied electrical charge. The applied electrical charge changes the orientation of the liquid crystals, affecting its transparency. For example, when the polarization direction of the light is parallel to the optical axis of the polarizers, light passes through the shutter 128, and when the polarization direction of the light is perpendicular, the shutter 128 blocks the light. Aspects of the disclosure may include other types of shutters, such as (but not limited to) microelectromechanical (MEMS) shutters, electrochromic optical shutters (ECOS), or mechanical shutters.

In some aspects, the viewing device 124 comprises a wireless transceiver and a battery (among other components) that allows communicative coupling between the viewing device 124 and the viewing device controller 122. The viewing device controller 122 controls operation of the viewing device 124. As one non-limiting example, the viewing device controller 122 controls operation of the shutter 128 (discussed in more detail below). In some aspects, the viewing device 124 comprises a cable (wired connection) that allows communicative coupling between the viewing device 124 and the viewing device controller 122.

In some instances, a user (e.g., a surgeon, medical staff, etc.) may be accustomed to wearing eyewear during a surgical procedure. For example, for neck and/or head surgery, some users prefer to wear loupes as they are stereoscopic, provide depth information, and allow the user to look down at his or her own hands instead of at a screen. Aspects of the disclosure may preserve the ergonomics offered by eyewear while providing fluorescent viewing capabilities, particularly with visible fluorescent dyes. The viewing device 124 may be used instead of, or in conjunction with, a capture device (e.g., comprising camera 114, and/or display 102) to view an image of the biological object 140. For example, a user may view a fluorescent light image through the viewing device 124, while medical staff views it through the display 102 (that displays the image of the biological object 140 captured by the camera 114).

The viewing device 124 may be any type of device suitable for viewing the biological object 140. Example viewing device 124 includes, but is not limited to, eyeglasses/goggles, loupes, or a corresponding clip-on device.

Figure 1D:
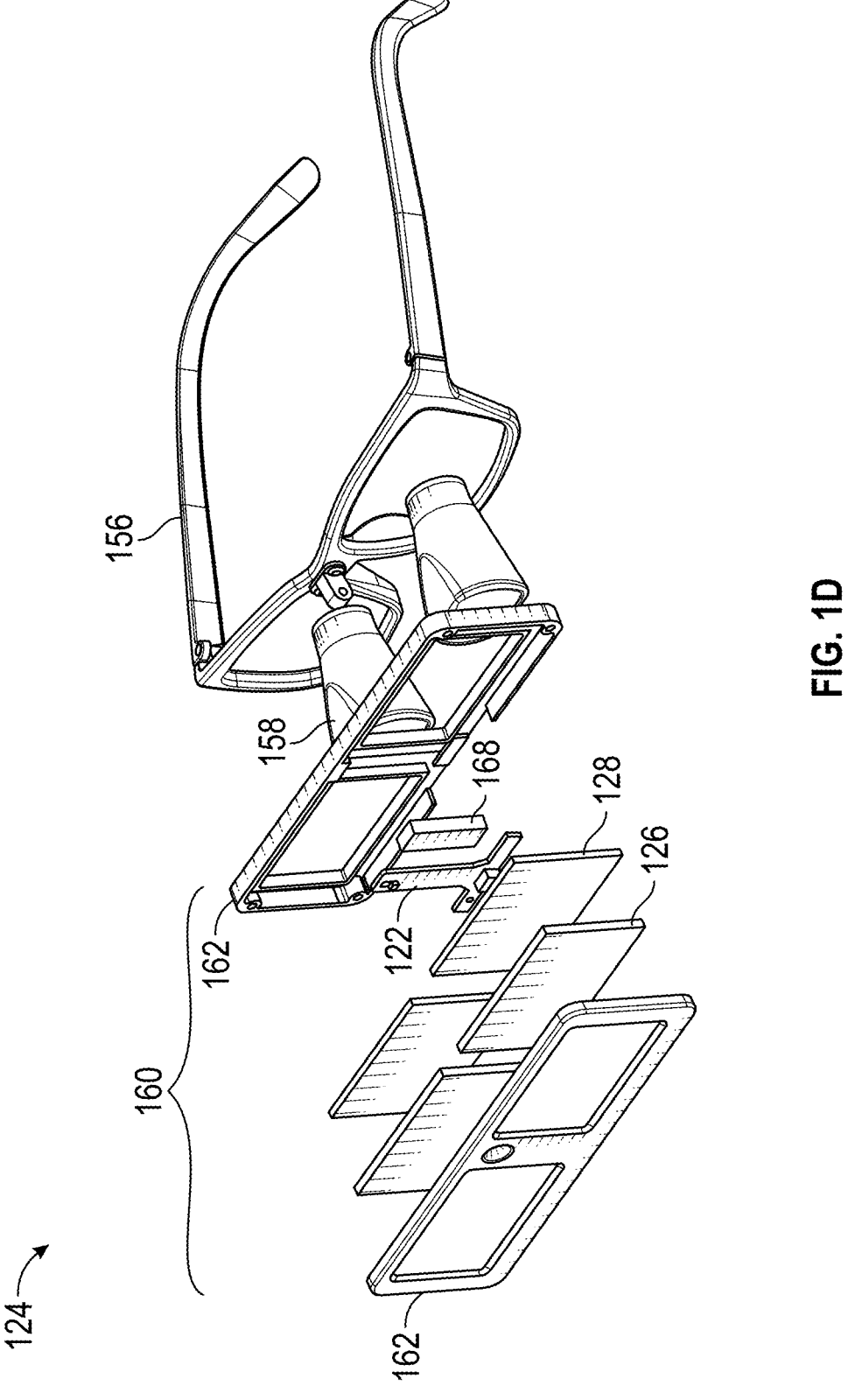

For example, as shown in FIG. 1C, the viewing device 124 may comprise glasses 156 and/or a clip-on device 160 that is located in front of loupes 158 when in use. The clip-on device 160 is located between the loupes 158 and the biological object 140. FIG. 1D illustrates a more detailed view of the clip-on device 160. In some aspects, the clip-on device 160 comprises housing 162, a filter 127, a shutter 128, a viewing device controller 122, and a battery 168. It is understood that the order of the components of the clip-on device 160 are not limited to the specific order shown in the figure, and aspects of the disclosure comprise other orders and configurations including, but not limited to, the clip-on device 160 comprising one or more lenses and/or the filter 127 located closer to the loupes 158 than the shutter 128.

Alternatively, the viewing device 124 may be used without a clip-on device 160, and one or more components for operation in the viewing mode(s) (e.g., filter 127, shutter 128, viewing device controller 122, battery 168) are included in the viewing device 124. For example, the components may be housed within glasses 156 and/or within loupes 158. In some aspects, the viewing device 124 may have any configuration suitable for viewing a biological object 140 illuminated with light (e.g., the viewing device 124 may not include or use loupes 158).

As another example, the viewing device 124 may comprise loupes 158 having a lens 126, a filter 127, and/or a shutter 128 disposed within (not shown), having any order and configuration suitable for viewing the biological object 140. The aspects and examples of the viewing device 124 disclosed herein may also be applied to a capture device that captures the image of the biological object 140 when the biological object 140 is illuminated with the light.

When open, the shutter 128 allows the user to view an image of the biological object 140. In some instances, the fluorescence may be weak, making it difficult for the user to visualize the fluorescent structures or tissue when the biological object 140 is illuminated with white light. The shutter 128, when closed, blocks the optical path, restricting light from entering the viewing device 124 and/or reaching the user's eye(s). The open time and/or close time of the shutter 128 may adjust the amount of background (e.g., illumination of the biological object 140 with white light) and the amount of fluorescence (e.g., illumination of the fluorophore with fluorescent light) seen by the user in an image of the biological object 140.

Additionally, in some examples, the viewing device 124 and the light source 130 are synchronized by way of the viewing device controller 122 generating synchronization signal(s), such as pulses transmitted to the light source controller 103. The light source controller 103 synchronizes the light source 130 with the viewing device 124. For example, the light source controller 103 may shift the timing of the white light pulse, the fluorescent light pulse, or both such that synchronization between the pulses of the synchronization signal(s) and the timing of the shutter 128 (e.g., in the viewing device 124) is optimized. In some aspects, the viewing device 124 may use the control signal(s) from the camera controller 112 to the light source controller 103 for synchronization. In some aspects, the synchronization may be by way of infrared light (e.g., an infrared light source is included in the light source 130), or cable or radio frequency (RF) communications.

The camera controller 112 controls operation of the camera 114. One or more of the camera controller 112, the camera 114, the light source controller 103, the light source 130, the viewing device controller 122, and/or the viewing device 124 may be communicatively coupled using a wired or wireless connection. In some aspects, the camera controller 112 is configured to control the shutter 128.

A viewing device 124 has a viewing mode comprising a white light mode, a fluorescent light mode, and an overlay mode (discussed in more detail below). In some aspects, the viewing device controller 122 operates the viewing device 124 (including a corresponding shutter 128) in accordance with the viewing mode. In some aspects, the open time of the shutter 128 varies based on the viewing mode. The viewing device 124 may be used to view a white light image when in white light mode, a fluorescent light image when in fluorescent light mode, and an overlay image when in overlay mode. In the white light mode, the biological object 140 is illuminated with white light and the viewing device 124 views a white light image of the biological object. In the fluorescent light mode, the biological object 140 is illuminated with fluorescent light for exciting a fluorophore, such as the fluorescent dye, in the biological object, and the viewing device 124 views a fluorescent light image emitted by the fluorophore in the biological object. An overlay image is an image of the biological object 140 when the biological object 140 is illuminated with both white light and fluorescent light, causing the overlay image to be an overlay of the white light image and the fluorescent light image. In some aspects, different parts of the viewing device 124 operate in different viewing modes; for example, the left lens 126 of the viewing device 124 may operate in white light mode, and the right lens 126 may operate in fluorescent light mode.

The viewing system 100 comprises a display 102 that displays an image of the biological object 140 captured by the camera 114. In some aspects, the image(s) captured by the camera 114 may be saved as an image file or a video. The viewing system 100 may also comprise one or more input devices that receive an input corresponding to the selection of the viewing modes. For example, a button (e.g., mechani-cal button or touchscreen button) may be pressed by a user to switch to a different viewing mode. In some aspects, a hands-free device (e.g., foot switch, voice command system, gesture control system, etc.) is used as an input device to ensure sterile operation.

In some aspects, the viewing system 100 comprises an input device (e.g., a knob) that receives an input corresponding to the settings of a viewing mode, such as the open time of the shutter 128. Adjusting the open time of the shutter 128 adjusts the amount of background included in the optical path and in the image. Different amounts of background may make the fluorescence become more or less visible in the image viewed by the user in overlay mode. In this manner, the amount of white light and the amount of fluorescent light in the optical path between the biological object 140 and the viewing device 124 may be dynamically adjusted. Other example settings that are dynamically adjustable include, but are not limited to, the illumination intensity of white light, the illumination intensity of fluorescent light, an on-time of a white light source, an on-time of a fluorescent light source, the close time of the shutter, an amount of white light in an overlay image, an amount of fluorescent light in an overlay image, the number of times the shutter 128 opens during a frame, etc.

Additionally or alternatively, the viewing system 100 sets one or more settings based on a user (e.g., surgeon, medical staff, or the like), the components of the viewing system 100 (e.g., viewing device 124, capture device, light source 130, etc.) or a profile. A profile comprises pre-determined electronically stored settings specific to a user (user profile), the components of the viewing system 100 (system profile), and/or operating room (operating room profile). For example, one user may prefer to view the tissue using overlay mode, while another user may prefer using fluorescent light mode. As another example, a user may prefer to see a greater amount of white light when visualizing tissue, whereas a different user may prefer to see a greater amount of fluorescence. These preferences may be saved in the respective user's profile (e.g., stored in storage 640 shown in FIG. 6). The viewing device controller 122 may automatically set the settings of the viewing mode based on the specific profile.

Aspects of the disclosure comprise a plurality of viewing devices 124, including a first viewing device 124 and a second viewing device 124. The second viewing device 124 views the image of the biological object 140 when the biological object 140 is illuminated with the light. The second viewing device 124 comprises a second shutter 128 that opens and closes in accordance with a second viewing mode of the second viewing device 124. The respective viewing modes of the different viewing devices 124 may be different from each other. For example, the first viewing device 124 may be operated in the overlay mode, while the second viewing device 124 may be operated in the fluorescent light mode at the same time. In some aspects, the plurality of viewing devices 124 may view the same biological object 140 illuminated by the same light source 130, thereby allowing one or more users to, e.g., simultaneously, view the biological object 140 in different viewing modes without requiring the use of additional light sources.

Figure 2:
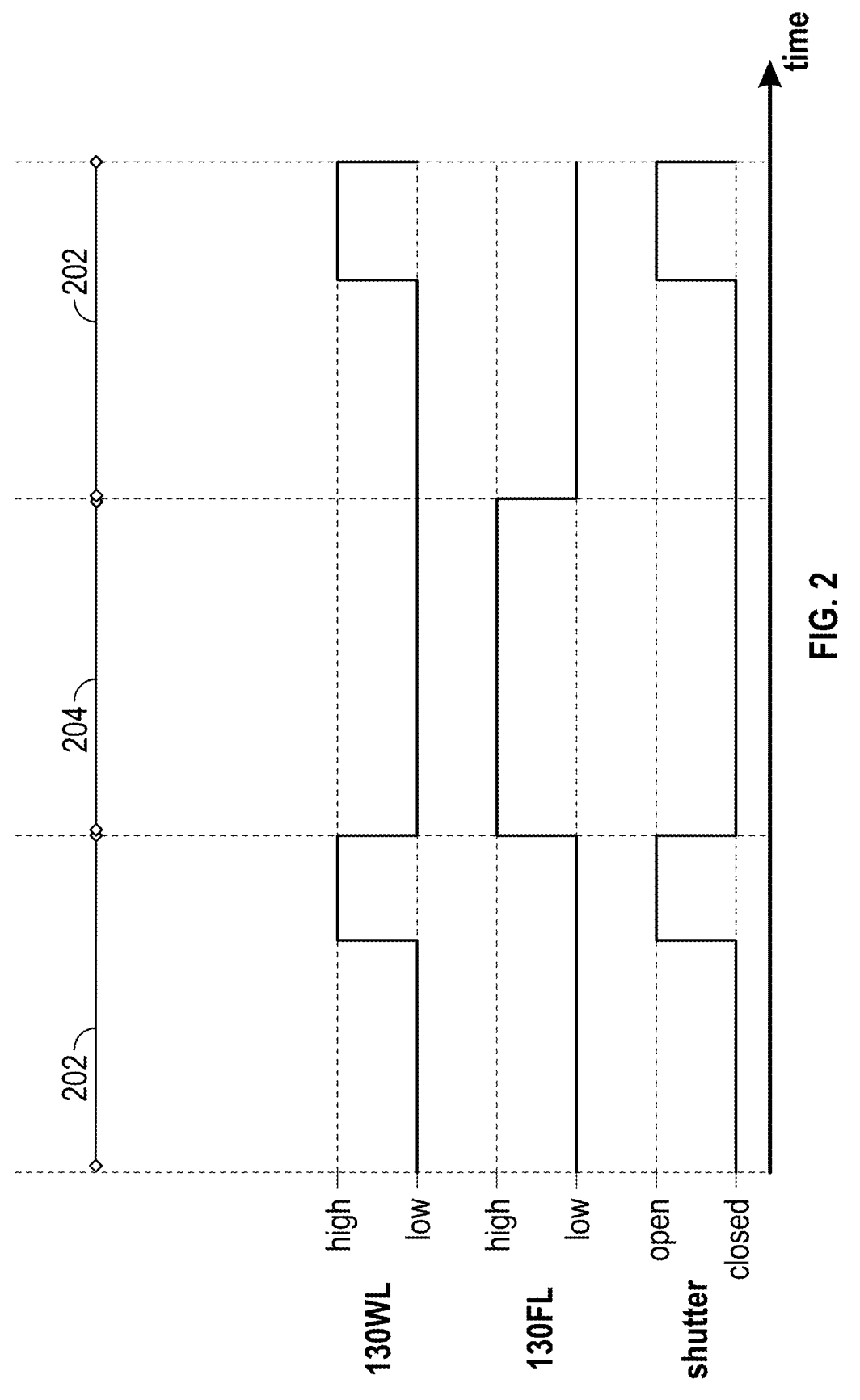
FIG. 2 illustrates an example timing diagram of a white light mode of a viewing system, according to some aspects.
Figure 3:
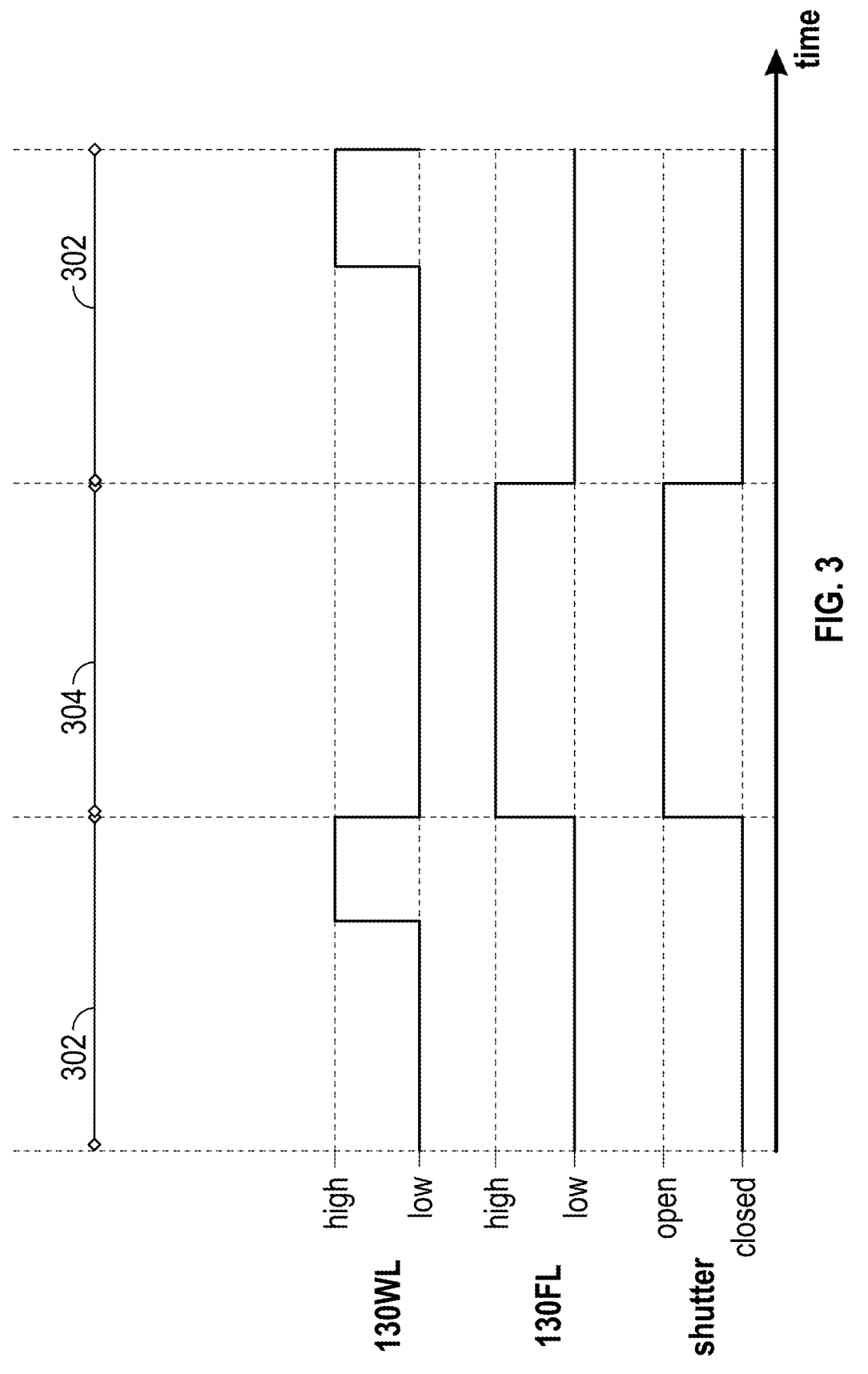
FIG. 3 illustrates an example timing diagram of a fluorescent light mode of a viewing system, according to some aspects.
Figure 4:
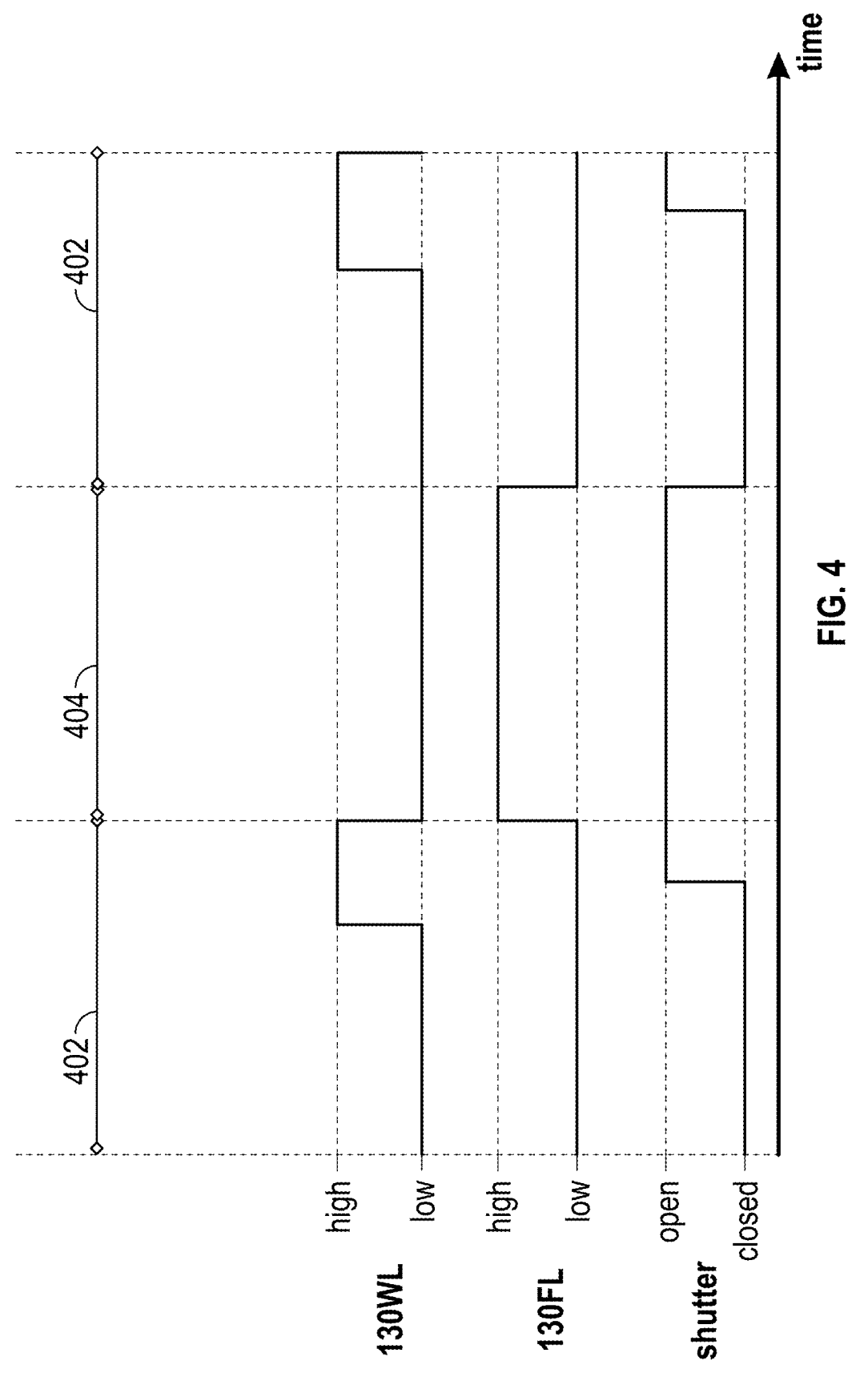
FIG. 4 illustrates an example timing diagram of an overlay mode of a viewing system, according to some aspects.

FIGS. 2-4 illustrate example timing diagrams of viewing modes of a viewing system 100, according to some aspects. As discussed above, the light source 130 may comprise a white light source 130WL and a fluorescent light source 130FL. The white light source 130WL illuminates white light (e.g., comprised of red, green, and blue light) during a white light pulse (e.g., white light pulse 202 of FIG. 2, white light pulse 302 of FIG. 3, and/or white light pulse 402 of FIG. 4), and the fluorescent light source 130FL illuminates fluorescent light (e.g., comprised of blue light) during a fluorescent light pulse (e.g., fluorescent light pulse 204 of FIG. 2, fluorescent light pulse 304 of FIG. 3, and/or fluorescent light pulse 404 of FIG. 4). During the white light pulse, the white light source 130WL is off for a first portion and then on for a second portion, while the fluorescent light source 130FL is off. During the fluorescent light pulse, the white light source 130WL is off, while the fluorescent light source 130FL is on.

Although the figures illustrate a frame comprising a white light pulse and a fluorescent light pulse, aspects of the disclosure include the duration of the white light pulse and/or the fluorescent light pulse being less than the duration of a frame. In some aspects, the duration of the white light pulse and/or the fluorescent light pulse may be equal to the duration of a frame. Additionally or alternatively, aspects of the disclosure comprise different durations for the portion of a light pulse that the light source is on and the portion of a light pulse that the light source is off. The duration(s) may be increased or decreased to adjust the appearance of the biological object 140 when viewed with the naked eye (e.g., without use of the viewing device 124), extend the lifetime of the light source 130, adjust the brightness of a viewing mode relative to another viewing mode (e.g., to reduce or avoid a noticeably visible change in brightness when switching from one viewing mode to another viewing mode), etc.

The viewing device 124 may comprise a shutter 128. The shutter 128 opens and closes in accordance with the viewing mode. FIG. 2 illustrates an example timing diagram for white light mode, according to some aspects. During the white light pulse 202, the shutter 128 is closed for the first portion of the white light pulse 202 and open for a second portion of the white light pulse 202. During the fluorescent light pulse 204, the shutter 128 is closed. To adjust the brightness of the white light, the on-time of the white light source 130WL and/or the open time for the shutter 128 may be increased. To decrease the brightness of the white light, the on-time of the white light source 130WL and/or the open time for the shutter 128 may be decreased.

FIG. 3 illustrates an example timing diagram for fluorescent light mode, according to some aspects. In fluorescent light mode, the shutter 128 is open during the fluorescent light pulse 304 and closed during the white light pulse 302.

FIG. 4 illustrates an example timing diagram for overlay mode, according to some aspects. Overlay mode comprises illuminating the biological object 140 with both white light and fluorescent light such that the viewed image appears as an overlay of a fluorescent light image over a white light image. Overlay mode comprises white light pulse 402 and fluorescent light pulse 404. In this example, during the white light pulse 402, the shutter 128 is closed for a first portion and open for a second portion. Here, in the fluorescent light pulse 404, the shutter 128 is open. In some aspects, the open time for the shutter 128 for white light pulse 402 is less than the on-time of the white light source 130WL. To increase the amount or percentage of white light visible within the overlay image, the on-time of the white light source 130WL and/or open time for the shutter 128 may be increased. To decrease the amount or percentage of white light visible within the overlay image, the on-time of the white light source 130WL and/or open time for the shutter 128 may be decreased.

Examples of the disclosure are not limited to the open and close times of the shutter 128 illustrated specifically in FIGS. 2-4. In some aspects, the open and/or close times of the shutter 128 may be adjusted according to the viewing mode. For example, when the portion of the white light pulse that the white light source 130WL is on increases, the open time of the shutter 128 may also increase to allow more white light in the optical path. More white light in the optical path causes the image to appear with a brighter background in overlay mode, for example. As another example, the open time of the shutter 128 may be decreased, so the image appears with a brighter fluorophore in the image in overlay mode due to less white light in the optical path. It is contemplated that, in some aspects, the open and/or close time of the shutter 128 includes an offset (e.g., the time when the shutter 128 opens or closes is shifted with respect to the light pulse) to synchronize the shutter 128 with one or more light pulses (white light pulse 402 and/or fluorescent light pulse 404).

Figure 5:
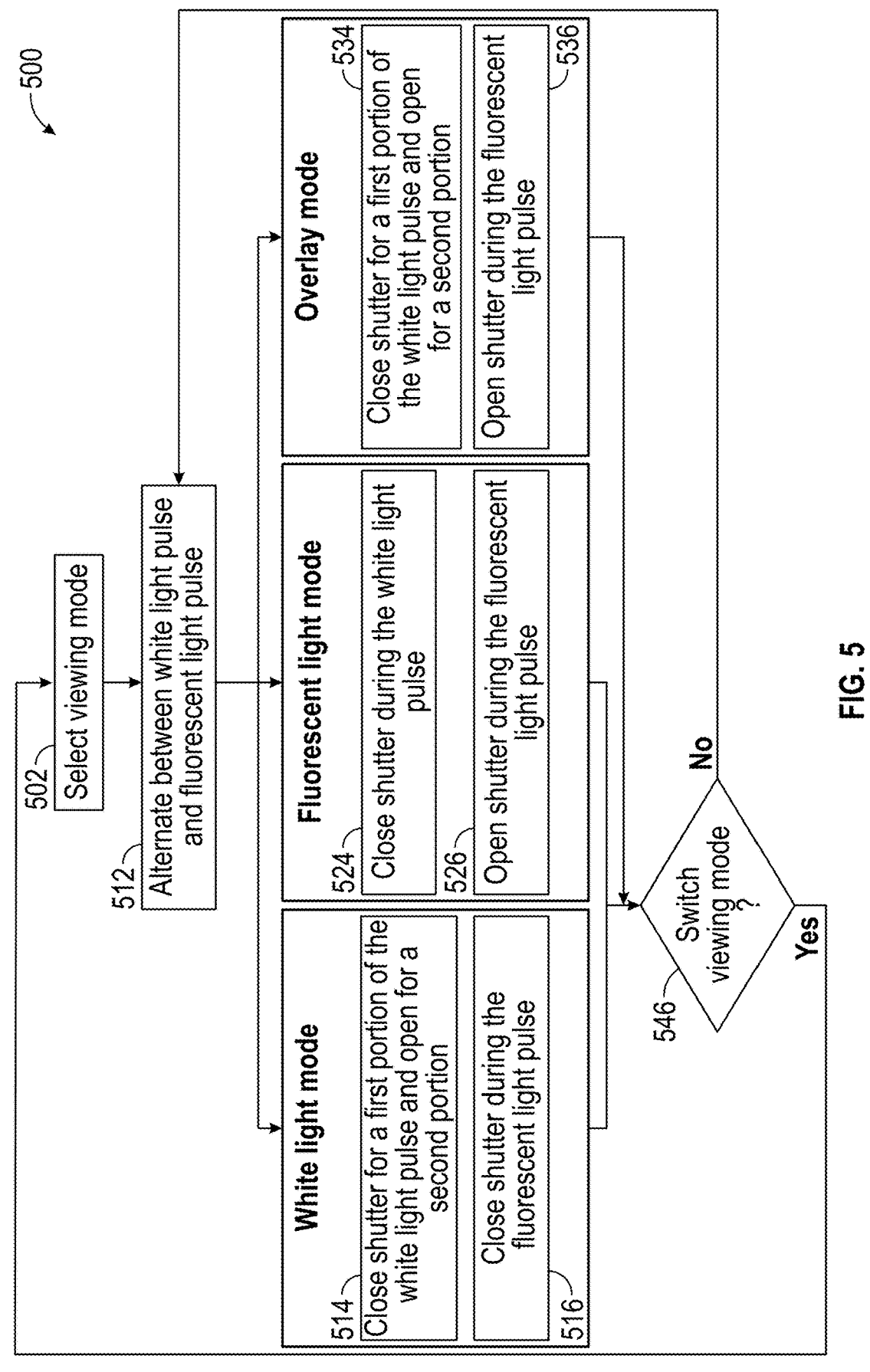
FIG. 5 illustrates a flowchart of an example method for viewing a biological object using a viewing system, according to some aspects.

FIG. 5 illustrates a flowchart of an example method for viewing a biological object using a viewing system, according to some aspects. Method 500 comprises selecting a viewing mode in step 502. Example viewing modes include, but are not limited to, white light mode, fluorescent light mode, and overlay mode. The viewing system 100 may receive the selected viewing mode via an input device, such as a foot switch or a database comprising a surgeon profile. In step 512, the viewing system 100 operates with a white light pulse (where the white light source 130WL is off and then on) and a fluorescent light pulse (where the fluorescent light source 130FL is on). In some aspects, during the white light pulse, the off-time of the white light source 130WL may be different (e.g., longer) than the on-time. A user may adjust the on-time by way of, e.g., a profile stored in a database, an input device (e.g., a knob), or another type of input.

If the selected mode is white light mode, then in step 514, during the white light pulse (e.g., white light pulse 202 of FIG. 2), the shutter 128 is closed for a first portion of the white light pulse and open for a second portion. In step 516, the shutter 128 is closed during the fluorescent light pulse (e.g., fluorescent light pulse 204 of FIG. 2). Although the figure illustrates steps 514 and 516 as separate steps, aspects of the disclosure comprise these steps as being performed as the same step and/or at the same time (e.g., steps 514 and 516 are simultaneous). Steps 514 and 516 may be repeated until the user switches viewing modes (step 546). In some aspects, the method 500 switches the viewing mode (step 546), e.g., in response to a corresponding selection from an input device.

In fluorescent light mode, during the white light pulse (e.g., white light pulse 302 of FIG. 3), the shutter 128 is closed (step 524), and during the fluorescent light pulse (e.g., fluorescent light pulse 304 of FIG. 3), the shutter 128 is open (step 526). Although the figure illustrates steps 524 and 526 as separate steps, aspects of the disclosure comprise these steps as being performed as the same step and/or at the same time (e.g., steps 524 and 526 are simultaneous). Steps 524 and 526 may be repeated until the user switches viewing modes (step 546).

For the overlay mode (timing diagram of FIG. 4), the shutter 128 is open when either light source 130 is on and closed when both light sources 130 are off. For example, the shutter 128 is closed for a first portion of the white light pulse (e.g., white light pulse 402 of FIG. 4) and open for a second portion (step 534). The shutter 128 is open during the fluorescent light pulse (e.g., fluorescent light pulse 404 of FIG. 4). In some aspects, opening the shutter 128 for the fluorescent light pulse 404, after the biological object 140 has been illuminated with white light in the white light pulse

402, adds background to the overlay image. Aspects of the disclosure comprise the steps: step 534 (closing the shutter 128 for a first portion of the white light pulse 402 and opening the shutter 128 for a second portion of the white light pulse 402) and step 536 (opening the shutter 128 during the fluorescent light pulse 404), being performed at the same time. The light pulses 402 and 404 (shown in FIG. 4) and corresponding steps may be repeated while the viewing system 100 is used in the overlay mode. Although FIG. 4 illustrates the shutter 128 as being open for a portion of the white light pulse 402 and a portion of the fluorescent light pulse 404, aspects of the disclosure include the shutter 128 opening and closing any number of times suitable for creating an overlay image. For example, the shutter 128 may open for a first portion of the white light pulse 402, close for a second portion of the white light pulse 402, and then open again for a third portion of the white light pulse 402 of a given frame.

In some aspects, the amount of time it takes for the shutter 128 to open may be different than the amount of time it takes for the shutter 128 to close. For example, it may take the shutter 128 longer to open (e.g., 1 millisecond) than it takes the shutter 128 to close (e.g., 0.05 milliseconds). The slower time for opening the shutters 128 may allow a small and/or gradual amount of white light in the optical path so that the white light does not dominate the overlay image. In some instances, the white light pulse 202, 302, 402 may not immediately precede and/or follow the fluorescent light pulse 204, 304, 404, respectively. For example, the white light pulse 202, 302, 402 and the fluorescent light pulse 204, 304, 404 may be separated by an ambient light pulse in between the white light pulse 202, 302, 402 and the fluorescent light pulse 204, 304, 404, where the amount of ambient light is measured and then removed from the image. In such instances, the open time and/or the amount of time it takes for the shutter 128 to open may be adjusted. In some aspects, the fluorescent light pulse 204, 304, 404, may precede the white light pulse 202, 302, 402.

Figure 6:
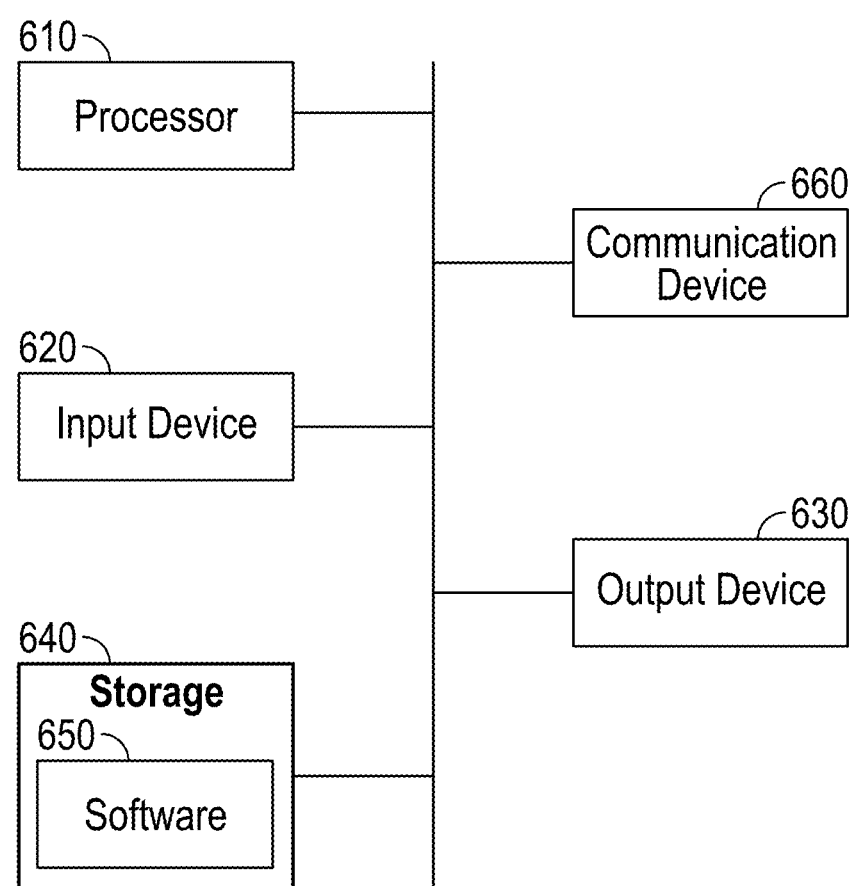
FIG. 6 illustrates an example computing system used for performing any of the methods and systems described herein, according to some aspects.

FIG. 6 illustrates an example computing system, in accordance with some examples, that can be used for performing any of the methods described herein, including method 500 of FIG. 5, and can be used for any of the systems described herein, including the viewing system 100 of FIG. 1. System 600 can be a computer coupled to a network, which can be, for example, an operating room network or a hospital network. System 600 can be a client computer or a server. As shown in FIG. 6, system 600 can be any suitable type of controller (including a microcontroller) or processor (including a microprocessor) based system, such as an embedded control system, personal computer, workstation, server, or handheld computing device (portable electronic device) such as a phone or tablet. The system can include, for example, one or more of processor 610, input device 620, output device 630, storage 640, or communication device 660.

Input device 620 can be any suitable device that provides input, such as a touch screen, keyboard or keypad, mouse, gesture recognition component of a virtual/augmented reality system, or voice-recognition device. Output device 630 can be or include any suitable device that provides output, such as a touch screen, haptics device, virtual/augmented reality display, or speaker.

Storage 640 can be any suitable device that provides storage, such as an electrical, magnetic, or optical memory including a RAM, cache, hard drive, removable storage disk, or other non-transitory computer readable medium. Communication device 660 can include any suitable device capable of transmitting and receiving signals over a network, such as a network interface chip or device. The components of the computer can be coupled in any suitable manner, such as via a physical bus or wirelessly.

Software 650, which can be stored in storage 640 and executed by processor 610, can include, for example, the programming that embodies the functionality of the present disclosure (e.g., as embodied in the devices as described above). For example, software 650 can include one or more programs for performing one or more of the steps of the methods disclosed herein.

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

System 600 may be coupled to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, cable networks, DSL, or telephone lines.

System 600 can implement any operating system suitable for operating on the network. Software 650 can be written in any suitable programming language, such as C, C++, C #, Java, or Python. In various examples, application software embodying the functionality of the present disclosure can be deployed in different configurations, such as in a client/server arrangement or through a Web browser as a Web-based application or Web service, for example.

The foregoing description, for the purpose of explanation, has been described with reference to specific aspects. However, the illustrative discussions above are not intended to be exhaustive or to limit the invention to the precise forms disclosed. Many modifications and variations are possible in view of the above teachings. The aspects were chosen and described in order to best explain the principles of the techniques and their practical applications. Others skilled in the art are thereby enabled to best utilize the techniques and various aspects with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A viewing system for viewing a biological object, the system comprising:
   a light source for illuminating the biological object with light, wherein the light source comprises a white light source; and
   a viewing device that views the biological object when the biological object is illuminated with the light, wherein the viewing device comprises a shutter that opens and closes in accordance with a viewing mode of the viewing device,
   wherein the viewing mode comprises:
      an overlay mode comprising the shutter being open during a first portion of a white light pulse, closed during a second portion of the white light pulse, and open during a fluorescent light pulse, wherein the white light source is on during the first portion of the white light pulse and off during the second portion of the white light pulse.

2. The system of claim 1, wherein the viewing device comprises glasses, one or more loupes, a microscope, or a corresponding clip-on device.

3. The system of claim 1, wherein the shutter is a liquid crystal shutter disposed within the viewing device.

4. The system of claim 1, wherein an open time of the shutter varies based on the viewing mode, and wherein the viewing mode further comprises a white light mode and a fluorescent light mode.

5. The system of claim 1, wherein, when the viewing mode further comprises:
   a white light mode, the shutter is open during a white light pulse and closed during a fluorescent light pulse; or
   a fluorescent light mode, the shutter is open during a fluorescent light pulse and closed during a white light pulse.

6. The system of claim 1, further comprising:
   a viewing device controller that controls operation of the viewing device, wherein the viewing device comprises a wireless transceiver that communicatively couples the viewing device and the viewing device controller.

7. The system of claim 1, wherein settings of the viewing mode are dynamically adjustable, the settings comprising one or more of: an illumination intensity of white light, an illumination intensity of fluorescent light, an on-time of the white light source, an on-time of a fluorescent light source, an open time of the shutter, a close time of the shutter, an amount of white light in an overlay image, an amount of fluorescent light in an overlay image, a number of times the shutter opens during a frame, or a combination thereof.

8. The system of claim 1, further comprising:
   a second viewing device that views the biological object when the biological object is illuminated with the light, wherein the second viewing device comprises a second shutter that opens and closes in accordance with a second viewing mode of the second viewing device,
   wherein the viewing mode of the viewing device is capable of being different from the second viewing mode of the second viewing device.

9. A method of viewing a biological object, the method comprising:
   illuminating, using a light source, the biological object with light, wherein the light source comprises a white light source;

viewing, by a viewing device, the biological object when the biological object is illuminated with the light; and
   opening and closing a shutter of the viewing device in accordance with a viewing mode of the viewing device, wherein the viewing mode comprises:
      an overlay mode comprising the shutter being open during a first portion of a white light pulse, closed during a second portion of the white light pulse, and open during a fluorescent light pulse, wherein the white light source is on during the first portion of the white light pulse and off during the second portion of the white light pulse.

10. The method of claim 9, wherein the viewing device comprises glasses, one or more loupes, a microscope, or a corresponding clip-on device.

11. The method of claim 9, wherein the shutter is a liquid crystal shutter disposed within the viewing device.

12. The method of claim 9, further comprising:
   adjusting an open time of the shutter based on the viewing mode, wherein the viewing mode further comprises a white light mode and a fluorescent light mode.

13. The method of claim 9, wherein, when the viewing mode further comprises:
   a white light mode, the shutter is open during a white light pulse and closed during a fluorescent light pulse; or
   a fluorescent light mode, the shutter is open during a fluorescent light pulse and closed during a white light pulse.

14. The method of claim 9, further comprising:
   dynamically adjusting settings for the viewing mode, wherein the settings comprise one or more of: an illumination intensity of white light, an illumination intensity of fluorescent light, an on-time of the white light source, an on-time of a fluorescent light source, an open time of the shutter, a close time of the shutter, an amount of white light in an overlay image, an amount of fluorescent light in an overlay image, or a number of times the shutter opens during a frame.

15. The method of claim 9, further comprising:
   viewing, using a second viewing device, the biological object when the biological object is illuminated with the light; and
   opening and closing a second shutter of the second viewing device in accordance with a second viewing mode of the second viewing device,
   wherein the viewing mode of the viewing device is capable of being different from the second viewing mode of the second viewing device.

16. A viewing device, comprising:
   a shutter configured to open and close in accordance with a viewing mode of the viewing device, wherein the viewing mode comprises:
      an overlay mode comprising the shutter being open during a first portion of a white light pulse, closed during a second portion of the white light pulse, and open during a fluorescent light pulse, wherein a white light source is on during the first portion of the white light pulse and off during the second portion of the white light pulse; and
   a connection configured to communicatively couple the viewing device and a viewing device controller, wherein the viewing device controller is configured to control operation of the shutter;
   wherein the viewing device is configured for viewing a biological object when the biological object is illuminated with light.

17. The viewing device of claim 16, comprising glasses, one or more loupes, a microscope, or a corresponding clip-on device.

18. The viewing device of claim 16, wherein the shutter is a liquid crystal shutter disposed within the viewing device.

19. The viewing device of claim 16, wherein an open time of the shutter varies based on the viewing mode, and wherein the viewing mode further comprises a white light mode and a fluorescent light mode.

20. The viewing device of claim 16, wherein, when the viewing mode further comprises:

a white light mode, the shutter is open during a white light pulse and closed during a fluorescent light pulse; or a fluorescent light mode, the shutter is open during a fluorescent light pulse and closed during a white light pulse.

* * * * *